United States Patent
Hauser

[11] Patent Number: 5,939,640
[45] Date of Patent: Aug. 17, 1999

[54] PRESSURE MEASUREMENT DEVICE, IN PARTICULAR FOR AN INFUSION APPARATUS

[76] Inventor: Jean-Luc Hauser, 1499 chemin S. Maymes, F-06600 Antibes, France

[21] Appl. No.: 08/170,224

[22] PCT Filed: Apr. 28, 1993

[86] PCT No.: PCT/FR93/00416

§ 371 Date: Jun. 9, 1994

§ 102(e) Date: Jun. 9, 1994

[87] PCT Pub. No.: WO93/22641

PCT Pub. Date: Nov. 11, 1993

[30] Foreign Application Priority Data

Apr. 29, 1992 [FR] France ................................ 92 05312
Apr. 28, 1993 [WO] WIPO .................... PCT/FR93/00416

[51] Int. Cl.$^6$ ........................................................ G01L 9/06
[52] U.S. Cl. ................................................................ 73/727
[58] Field of Search ................................ 73/706, 861.24; 128/635

[56] References Cited

U.S. PATENT DOCUMENTS

| | | |
|---|---|---|
| 3,239,696 | 3/1966 | Burkhalter et al. . |
| 4,431,425 | 2/1984 | Thompson et al. . |
| 4,446,344 | 5/1984 | Fiedler . |
| 4,559,832 | 12/1985 | Burlage et al. ...................... 73/861.24 |
| 4,993,265 | 2/1991 | Koen et al. .............................. 73/706 |
| 5,117,827 | 6/1992 | Stuebe et al. ............................ 128/635 |
| 5,209,125 | 5/1993 | Kalinoski et al. .................... 73/861.24 |

FOREIGN PATENT DOCUMENTS

| | | |
|---|---|---|
| 2461424 | 7/1976 | Germany . |
| 2809264 | 9/1979 | Germany . |
| 2012052 | 7/1979 | United Kingdom . |

OTHER PUBLICATIONS

IEEE Transactions on Electron Devices, vol. ED26, No. 12, Dec. 1979; J.M. Borky et al; "Integrated Signal Conditioning for Silicon Pressure Sensors".
Patent Abstracts of Japan; vol. 7, No. 10 (P–168); Pressure Wave Sensor; Rikoo Tokei K.K.
Siemens Forschungs–Und Entwicklungsberichte; V. 10, No. 2, 1981; pp. 72–77; F. Breimesser et al; "Piezoresistive Pressure Sensor With Silicon Diaphragm".
Soviet Inventions Illustrated; Week 8726, Jul. 6, 1993; SU 1270–593–A.

*Primary Examiner*—George Dombroske
*Assistant Examiner*—Jewel V. Thompson
*Attorney, Agent, or Firm*—Francis A. Sirr; Earl C. Hancock; Holland & Hart LLP

[57] ABSTRACT

A device for measuring the pressure in an infusion tube (12), including a pressure sensor (20) and a housing (14) comprising at least one chamber (16) with one side defined by a deformable membrane (18) contacting the wall of the infusion tube, and containing said sensor. A fluid (24) is provided between the membrane (18) and the sensor (20). The fluid is non-liquid and has a Poisson ratio of at least 0.49 as well as an instantaneous modulus of elasticity of under 10 MPa so that the sensor response curve is linear. The device may be used in an infusion apparatus, particularly a portable infusion apparatus.

7 Claims, 1 Drawing Sheet

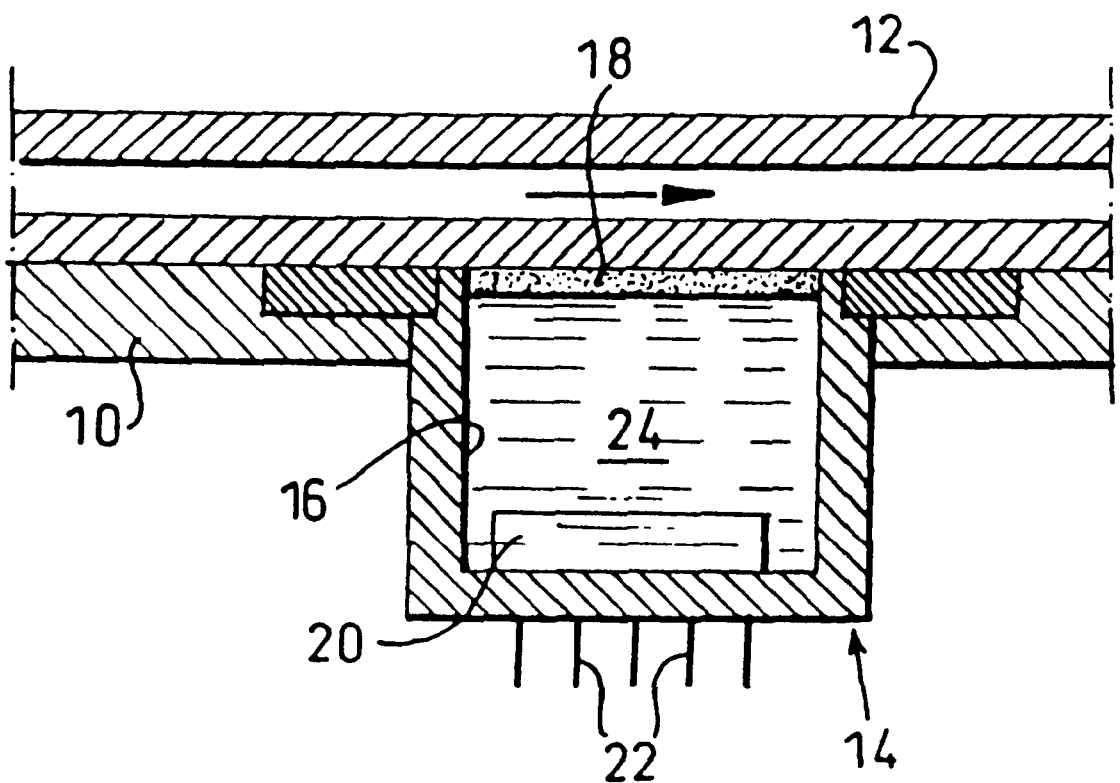

PRESSURE MEASUREMENT DEVICE, IN PARTICULAR FOR AN INFUSION APPARATUS

BACKGROUND OF THE INVENTION

1. Field of the Invention

This invention concerns pressure sensors and in particular their application to a pressure monitoring device in an infusion apparatus.

2. Description of Prior Art

Infusion pumps are used to inject medicamentous substances into a patient's body, usually intravascularly, but equally by other appropriate access channels.

It is useful to be able to monitor the flow pressure of the fluid as it comes down from the infusion pump, so as to detect any possible anomaly in the apparatus in operation. Indeed, various incidents may occur: the pump may race or adversely stop working, the catheter through which the medicamentous substance is injected may progressively close up with blood deposits, the infusion tube may be plicated, a leak may occur at any point in the infusion tube, etc . . .

Switches are currently used to monitor flow pressure in an infusion tube, but they work as a two-way system (on or off) and are activated by a substantial variation in pressure in relation to the nominal operating pressure. Such devices are not very precise, with measurement precision being of the order of 50% of the value of measured pressure. They are often used simply to control the shutting down of the motor driving the pump when the pressure exceeds a certain level.

Other more sophisticated devices are also known, such as those described in patents U.S. Pat. No. 4,446,344 and U.S. Pat. No. 4,431,425. The devices described in said patents comprise switches capable of not only stopping the motor when the pressure is too high but also restarting the motor once the pressure has descended to an acceptable value. However, there still remains the disadvantage of insufficient precision.

A device specially designed for the medical field is described in patent DE-A-2,461,424. Said device consists of a chamber filled with glycerine which transmits pressure to a sensor, said pressure being exerted on the wall of the sensor's chamber. Such a device with liquid (glycerine) as a pressure transmission fluid is difficult to use for measuring pressure in an infusion tube. Indeed, so that there may be an instantaneous reaction to variations of pressure in an infusion tube, it is necessary for the transmission fluid response to be linear, and such is not the case of liquid.

SUMMARY OF THE INVENTION

The purpose of this invention therefore is to propose a pressure measurement device which enables continuous and sufficiently precise measurement of fluid contained in an infusion tube.

Another purpose of the invention is to create a pressure measurement device in an infusion tube using a sensor with a linear response curve which reacts to variations in pressure.

The object of the invention therefore is a pressure measurement device consisting of a pressure sensor, a housing comprising at least one chamber with one side defined by a deformable membrane contacting the wall of the infusion tube and containing said sensor, with a fluid between the membrane and the sensor. Said fluid is non-liquid and has a Poisson ratio of at least 0.49 as well as an instantaneous modulus of elasticity of under 10 MPa so that the sensor response curve is linear.

In conformity with another characteristic, the fluid is a silicone gel.

DESCRIPTION OF THE PREFERRED EMBODIMENTS

Other characteristics and advantages of the invention shall become apparent in the following description given with references to the appended diagram which is presented purely as an example and provides a cross-section, schematic view of a sensor according to the invention, associated with an infusion tube.

In the diagram, part of an infusion apparatus is schematically represented comprising a pump with part 10 of its housing from which an infusion tube 12 is supplied which may be made of silicone, for example. A device according to this invention is used to continuously measure flow pressure in an infusion tube.

Said device comprises a housing 14 defining at least one chamber 16 with one of its walls formed by a deformable membrane 18. Said membrane may be made of elastomeric material or metal. Its elasticity may be derived from the nature of the material used or from the form given to the membrane. Said membrane may thus be formed by metal expansion bellows. It may be flat, or have a cylindrical concave form to fit an infusion line, or slightly rounded on the outside to increase the sensitivity of the measurement device. It is fixed to the housing by any appropriate means.

A standard piezoelectric sensor 20 is situated on the floor of the chamber 16 and must be of a suitable type, ie. resistive or capacitive, for measuring absolute or relative pressure.

By way of an example, such a sensor might include a silicon plate associated with an electrical Wheatstone bridge circuit, comprising, for instance, five connection conductors 22.

A fluid 24 is situated between the membrane and the piezoelectric sensor. The role of said fluid is absolutely essential as it maintains the transmission of pressure from the membrane 18 to the piezoelectric sensor 20. An instantaneous reaction is essential to any variation of pressure in the infusion tube which might, among other things, put the patient at risk. Said instantaneous reaction requires a linear sensor response, as any deviation in the response curve is difficult to interpret with a non-linear response. So as to satisfy said linearity requirement, the fluid in the chamber must be incompressible or near incompressible with a very low modulus of elasticity. Such a substance, which cannot be a liquid, must therefore have a Poisson ratio of no less than 0.49, an instantaneous modulus of elasticity of under 10 MPa, and a viscosity of the order of several hundred centipoises.

An example of such a substance might be a silicone gel such as that applied to a patient's skin to transmit an ultrasound signal from a transducer through the patient's body. As examples we cite "Silicone gel System Q7-2218" by Dow Corning and "Silicone gel System Q7-2167" by the same company, associated with "Silicone gel System Q7-2168".

Such a device is particularly suitable for use with a portable infusion pump given the slightness of its size and weight and the fact that it enables continuous measurement, which is precise, reliable and linear, of the changes in pressure coming down from the pump.

Precision may be of the order of 1% of the value of the measured pressure. The measurement is linear due to the use of a piezoelectric sensor and of a material suitable for transmitting variations of pressure from the membrane to said sensor.

The device according to this invention enables detection of any absence of liquid in the infusion tube, in the event of a leak or an empty container.

the device according to this invention enables monitoring of pressure variations in the infusion apparatus. In the event of progressive obstruction due to blood deposits in a vascular catheter, the device according to this invention enables detection of the corresponding increase in pressure. Warning is thus given before the catheter is completely obstructed enabling timely cleaning of the tube. In this way, explantation and replacement of the catheter is avoided.

Such a device may be associated with an electronic control unit which operates the overall functioning of the pump. The information provided by the sensor is then used to control and adapt the flow from the pump, something that standard two-way switches do not do.

Among the other advantages of this device, it may be noted that the sensor is not in direct contact with the fluid contained in the infusion tube.

I claim:

1. A pressure measurement device for measuring the pressure within an infusion tube (12) as a medicamentous substance flows through the infusion tube by operation of an infusion pump that is connected to the infusion tube, said device comprising;

a pressure sensor (20), a housing (14) comprising at least one chamber (16) with one side of said chamber being defined by a deformable membrane (18) contacting a wall of the infusion tube, and said chamber containing said sensor at a location within said chamber that is spaced from said membrane, and a fluid (24) within said chamber between said membrane (18) and said sensor (20), said fluid being nonliquid, said fluid having a Poisson ratio of at least 0.49, and said fluid having an instantaneous modulus of elasticity of under 10 MPa, so that said sensor has a linear pressure response curve.

2. The device according to claim 1 wherein said sensor is a piezoelectric sensor.

3. The device according to claim 1 or 2, wherein said fluid (24) has a viscosity of the order of several hundred centipoises.

4. The device according to claim 1, wherein said fluid is a silicone gel.

5. The device according to claim 4, wherein said deformable membrane (18) is cylindrical convex in form.

6. The device according to claim 4 wherein said fluid (24) has a viscosity of the order of several hundred centipoises.

7. The device according to claim 6 wherein said sensor (20) is a piezoelectric sensor.

* * * * *